(12) United States Patent
Straub et al.

(10) Patent No.: US 8,920,933 B2
(45) Date of Patent: Dec. 30, 2014

(54) AUTOXIDISABLE AQUEOUS COATING COMPOSITIONS

(75) Inventors: Hugues Straub, Wintzenheim (FR); Manish Sarkar, Widmer End (GB); Barry Norman Osborn, Hatfield (GB); James Stephen Wixey, Glastonbury (GB)

(73) Assignee: Akzo Nobel Coatings International B.V., Arnhem (NL)

( * ) Notice: Subject to any disclaimer, the term of this patent is extended or adjusted under 35 U.S.C. 154(b) by 338 days.

(21) Appl. No.: 13/377,338

(22) PCT Filed: Jun. 15, 2010

(86) PCT No.: PCT/EP2010/058338
§ 371 (c)(1),
(2), (4) Date: Feb. 17, 2012

(87) PCT Pub. No.: WO2010/146028
PCT Pub. Date: Dec. 23, 2010

(65) Prior Publication Data
US 2012/0149803 A1 Jun. 14, 2012

(30) Foreign Application Priority Data

Jun. 17, 2009 (EP) .................................. 09162889

(51) Int. Cl.
| | | |
|---|---|---|
| *B32B 27/30* | (2006.01) | |
| *C09D 5/02* | (2006.01) | |
| *C09D 147/00* | (2006.01) | |
| *B23B 27/00* | (2006.01) | |
| *C07K 14/655* | (2006.01) | |
| *C07K 14/65* | (2006.01) | |
| *A61K 38/00* | (2006.01) | |

(52) U.S. Cl.
CPC ................ *C09D 5/02* (2013.01); *C09D 147/00* (2013.01); *B23B 27/00* (2013.01); *C07K 14/655* (2013.01); *C07K 14/65* (2013.01); *A61K 38/00* (2013.01)
USPC .......................................... 428/500; 524/832

(58) Field of Classification Search
None
See application file for complete search history.

(56) References Cited

U.S. PATENT DOCUMENTS

| | | | |
|---|---|---|---|
| 4,206,099 A | 6/1980 | Bentley et al. | |
| 4,294,735 A | 10/1981 | Bentley et al. | |
| 5,712,339 A * | 1/1998 | Guerin et al. | 524/515 |
| 2008/0269411 A1 * | 10/2008 | Sarkar et al. | 524/853 |

FOREIGN PATENT DOCUMENTS

| | | |
|---|---|---|
| DE | 28 18 094 | 11/1978 |
| DE | 28 18 102 | 11/1978 |
| EP | 0 297 781 | 1/1989 |
| GB | 1 312 083 | 4/1973 |
| WO | 2006/013061 | 2/2006 |

OTHER PUBLICATIONS

International Search Report for PCT/EP2010/058338, dated Aug. 20, 2010, 4 pages.

* cited by examiner

*Primary Examiner* — Michael J Feely
(74) *Attorney, Agent, or Firm* — Kenyon & Kenyon LLP

(57) ABSTRACT

An autoxidisable aqueous varnish composition comprising: a) film forming polymer latex binder system comprising, on a non-vol basis, i) 40-60 wt % soft autoxidisable polymer particles of Fox Tg less than 5° C., ii) 60-40 wt % hard polymer particles of Fox Tg at least 40° C. wherein the soft autoxidisable polymer particles comprise at least 60 wt % gel b) a carrier liquid comprising at least 50 wt % water and an amount of a volatile organic material of from 0 to 2 wt % when calculated on the total liquid varnish composition, c) optionally pigment at a pigment to binder weight ratio up to 0.05:1 calculated on a non-vol basis.

18 Claims, No Drawings

AUTOXIDISABLE AQUEOUS COATING COMPOSITIONS

REFERENCE TO RELATED APPLICATIONS

This application is the U.S. National Phase of PCT/EP2010/058338 filed on Jun. 15, 2010, and claims the benefit of EP Application No. 09162889.1, filed on Jun. 17, 2009.

This invention relates to aqueous coating compositions of low to zero organic solvent content, in particular to unpigmented such compositions known as varnishes and clearcoats especially for coating wooden substrates, for example furniture and doors and even more especially for use in interiors.

The term 'varnish' is normally applied to transparent coating compositions containing little or no pigment and which are used to coat wood, including furniture, where the varnish is used to enhance the natural beauty of the wood grain.

Whilst in most territories furniture production is largely industrialised, in some it is more of a small scale industry. Furthermore, furniture restoration and refurbishment is also carried out in small workshops and even in the home by both skilled craftsmen and amateurs.

In most applications, the time for the coating to become hard enough to be handled is an important factor in its suitability for the job. In the home, for example, recently painted furniture will be expected to be usable again within say, 3-4 hours. Similarly in a factory environment, painted items will be moved from the painting area to a storage area without causing damage to the paint. Furthermore, in some circumstances, especially when painting furniture with a varnish for example, multiple coats are required to achieve the final lustrous appearance that customers desire. This requires that the earlier coat is sanded before the subsequent one is applied. Thus, the ability to sand the paint within a minimum time after application is an important property, especially for varnishes and clearcoats, which, because of their very low or indeed zero pigment content, are especially difficult to sand.

Coating compositions typically comprise a liquid carrier medium and a film forming binder polymer together with other components such as additives and pigments. Varnishes are a class of transparent coating which contain very low levels of pigments, in most instances have none at all. Some pigments are added for colour, whilst others are added to control the level of gloss of the coating.

The liquid carrier can comprise water or organic solvent or indeed a mixture of the two. The liquid carrier of aqueous or waterborne coatings comprise more than 50 wt % water and are usually formulated using binder polymers in dispersion, also known as latices. These comprise polymer particles dispersed in aqueous medium.

For a coating to be handleable and sandable at ambient temperature requires that it is formulated using a polymer having a glass transition temperature, Tg, which is higher than the ambient temperature and preferably, higher than the temperature the coating reaches during sanding. However such polymer particles will not form a continuous film unless the ambient temperature is raised above the Tg of the polymer or a coalescing solvent is used. Neither of these options is particularly desirable However, in order for such aqueous coatings to form continuous films at ambient temperatures of from 3 to 40° C., and which are hard when dry, large amounts of coalescing solvent, sometimes referred to as plasticiser, are required. Unfortunately, such solvent must be chosen not only for its coalescing effect on the latex particles to facilitate film formation, but also its high volatility. This enables it to escape the film leaving behind a hard coat of varnish. Of course, such volatility releases organic solvent to the atmosphere increasing the volatile organic content (VOC) of the coating. It is impossible, using such an approach, to make a paint that film forms in this way and yet contain little or no coalescing solvent at all.

European Application EP 1776431 discloses coatings based on microgel particles. However, there is no teaching as to how to formulate a varnish which is easy to sand and can be recoated within 4 hours, especially when starting from a polymer of Tg below 5° C.

A further deficiency of coatings formulated in this way is that they cannot be sanded within a reasonable time of 4 hours.

Increasingly, legislation and industry codes of practice require that the amount of volatile organic liquid is reduced to a minimum. Coatings containing less than 10 wt % organic solvent are known.

We have now found coating compositions that overcome the deficiencies of the known prior art.

The present invention provides an autoxidisable aqueous varnish composition comprising a) film forming polymer latex binder system comprising, on a non-vol basis i) 40-60 wt % soft autoxidisable polymer particles of Fox Tg less than 5° C.

ii) 60-40 wt % hard polymer particles of Fox Tg at least 40° C. wherein the soft autoxidisable polymer particles comprise at least 60 wt % gel b) a carrier liquid comprising at least 50 wt % water and an amount of a volatile organic material of from 0 to 2 wt % when calculated on the total liquid varnish composition c) optionally pigment at a pigment to binder weight ratio up to 0.05:1

The term gel is used to identify polymer that is insoluble in tetrahydrofuran as determined according to the test method described below.

The autoxidisable capability of the soft particles is preferably provided by autoxidisable monomers copolymerised into the polymer of the particles. A preferred method of producing such monomers is to form an adduct of an autoxidisable fatty acid with an ethylenically unsaturated monomer reactive with the fatty acid. Glycidyl methacrylate is one such monomer where by reaction of the oxirane moiety with the carboxyl moiety of the acid, an autoxidisable monomer is formed which is copolymerisable with other ethylenically unsaturated monomers. Preferably, the autoxidisable capability is provided by an adduct of glycidyl methacrylate and unsaturated fatty acid.

Such fatty acids are autoxidisable because they contain unsaturated double bonds capable of reacting with atmospheric oxygen.

The autoxidisable capability is (preferably) provided by unsaturated fatty acids derived from plant and animal oils. Fatty acids derived from plant oils are preferably used as they are a renewable resource.

Fatty acids derived from natural sources, such as oils, inevitably comprise a mixture, including some saturated fatty acids, as shown below. In addition the composition of the mixture may itself vary according to the geographic source of the parent oil. Some indicative compositions are shown below.

|  |  | Tall oil fatty acid | Linseed oil | Soya oil |
|---|---|---|---|---|
| Palmitic acid | ($C_{16}$, 0) | 3 | 6 | 10 |
| Stearic acid | ($C_{18}$, 0) | 0 | 2.5 | 4 |
| Arachidic | ($C_{20}$, 0) | 0 | 0.5 | 0 |
| Oleic acid | ($C_{18}$, 1) | 29 | 19 | 23 |
| Linoleic | ($C_{18}$, 2) | 64* | 24.1 | 51 |
| Linolenic | ($C_{18}$, 3) | 0 | 47.4 | 7 |
| Rosin | (abietic acid) | 1.6 | 0 | 0 |
| Other |  | 2.4 | 0.5 | 5 |
| Saturated |  | 3 | 9 | 14 |
| Unsaturated | (total) | 93 | 90.5 | 81 |
| Unsaturated | (>1) | 64 | 71.5 | 58 |
| Iodine value |  | 145-165 | 155-205 | 118-144 |

*actually 57% non-conjugated and 7% conjugated

The subscript refers to the carbon chain length of the fatty acid and 0, 1 or 2 indicates the number of ethylenically unsaturated bonds in the fatty acid.

Advantageously, the fatty acid should contain at least two double bonds and even more preferably at least some should be conjugated. By conjugated is meant that the double bonds are separated by one carbon-carbon bond only.

As the commercially available fatty acids are derived from natural materials, as discussed above, they tend to be mixtures of fatty acids containing mono-, di- and even tri-unsaturated bonds with varying degrees of conjugation. Preferably, the minimum amount of conjugated unsaturated fatty acid in the fatty acid mixture, calculated on a weight basis, is 1.5%, more preferably from 1.5 to 15%, even more preferably from 2 to 10% and most preferably from 5 to 10%. The maximum amount of conjugated unsaturated fatty acid in the mixture can be up to 100%, in principle, but this is unlikely to be commercially viable in all but the most specialised applications due to the high cost. In practice, the upper limit is up to 60 to 80%.

Suitable examples of fatty acids for use in the present invention include those derived from linseed oil, tung oil, soybean oil, menhaden oil, tall oil, dehydrated castor oil. More preferred are the tall oil fatty acids; that is fatty acids derived from tall oil, even more preferably those derived from tall oil containing rosin (mainly abietic acid), even more preferred are the acids derived from tall oil containing at least 0.5 wt % rosin and most preferred is tall oil containing from 0.5 to 4 wt % rosin. The presence of the rosin increases the amount of gel in the soft polymer. Sylfat 2 is a suitable such material.

The preferred acids include the $C_{10}$-$C_{24}$ unsaturated drying or semi-drying acids such as oleostearic, linoleic, linolenic, oleic and arachidonic fatty acids.

The glass transition temperature Tg, can be calculated using the Fox equation.

The polymer particles are prepared as aqueous dispersions, also known as latices, by polymerising ethylenically unsaturated monomers including esters of acrylic and/or methacrylic acid, also referred to as acrylic monomers. Vinyl monomers and styrenic monomers can also be used.

Examples of acrylic monomers which may be used to produce the polymers for use in this invention include acrylic or methacrylic acid esters such as methyl(meth)acrylate, ethyl(meth)acrylate, propyl(meth)acrylate, butyl(meth)acrylate, 2-ethylhexyl(meth)acrylate, decyl(meth)acrylate, hydroxyethyl(meth)acrylate, and hydroxypropyl(meth)acrylate; alkenes such as ethylene and propylene; and polymerizable carboxylic acids such as acrylic acid, methacrylic acid, itaconic acid, maleic acid and fumaric acid.

Examples of other suitable vinyl monomers which may be employed include acrylonitrile; dienes such as 1,2-butadiene, 1,3-butadiene and chloroprene; 1,3,5-hexatriene; styrenic monomers such as styrene, alpha-methyl styrene, vinyl toluene; vinyl carboxylate esters such as vinyl acetate; vinyl versatate; vinyl halides such as vinyl chloride and vinylidene chloride.

Copolymerised styrene and its homologues have the additional advantage of being particularly active in generating and coupling to free radicals and so they promote autoxidation thereby reducing the time taken for the coating properties to develop.

Preferred monomers include acrylic acid, methacrylic acid, acrylic acid and methacrylic acid esters of aliphatic or aromatic alcohols, styrene, substituted styrenes, vinyl acetate and other vinyl carboxylate esters.

Other monomers that may be used include α-olefins such as ethylene, propylene or butene-1 and styrene or its homologues.

As a further embodiment of the present invention the soft autoxidisable polymers of this invention can also comprise amide containing alpha, beta unsaturated monomers. Preferably, the soft polymer comprises up to 6 wt % of an amide monomer, more preferably from 2 to 6 wt %, even more preferably from 3 to 5 wt % and most preferably from 3.5 to 4.5 wt %. They provide crosslinking through hydrogen bonding and appear to enhance the crosslinking resulting from autoxidation. This has been found to further increase both the attainment of early hardness, for example at one day, and the film properties of the dispersions. Examples of such amide containing unsaturated monomers include acrylamide, methacrylamide and alkoxy acrylamides and methacrylamides such as N-butoxy methacrylamide. Most preferred is methacrylamide.

The soft polymer particles must comprise at least 60 wt % gel as determined by the test method described hereinbelow. This level of gel is necessary in order to achieve sandability within the required four hours.

A preferred way to achieve this is to copolymerise the autoxidisable monomer described above with a required selection of the ethylenically unsaturated acrylic, vinyl and/or styrene monomers as described above. Preferably, at least 30 wt %, more preferably, from 30 to 65 wt % and still more preferably from 40 to 50 wt % of the total monomer composition should be the autoxidisable monomer.

Chain transfer agents can be added at low levels to the monomer mixture to control the molecular weight of the soft polymer. However, the amount used must not be so high that the gel content falls below the required amount of 60 wt % as hereinbefore described.

The soft polymers particles are typically prepared by free radical mini-emulsion polymerisation with the monomers pre-emulsified in an aqueous medium, preferably water. In mini-emulsion polymerisation, the monomers are pre-emulsified in water, in the presence of surfactants and a hydrophobic component, usually using high shear to form small, uniform droplets. Preferably, the mean droplet size is less than 500 nm in diameter, more preferably less than 300 and most preferably from 0.05 to 150 nm.

Without wishing to be bound by this it is thought that the hydrophobic component stabilises the droplets and prevents their coalescence into larger droplets over time Hexadecane can be used, or more preferably the long chain unsaturated fatty acid adduct already present in the system can act as hydrophobe and stabilise the mini-emulsion.

The required high shear agitation may be provided by mechanical emulsifiers such as a Ross 100 (available from Ross and Son, Hauppauge, N.Y., USA) or a Silverson (available from Silverson machines Ltd, Chesham, Buckinghamshire, UK) or an IKA emulsifier (available from IKA-Works Inc, Cincinnati, Ohio, USA). Alternatively, a Sonolator (available from Sonic Corp, Stratford, Conn., USA) may be used which employs ultrasound to generate the required shear. Preferably, agitation is sufficiently energetic to produce eventual particles of miniemulsion which have a number average particle size of below 500 nm and preferably below 300 nm.

A redox initiator system, advantageously water soluble, is preferably used. In such systems the initiators are used in conjunction with a suitable reducing agent and a compound that reversibly changes oxidation state. Examples of reducing agents include reducing sugars, sodium formaldehyde sulfoxylate, sodium metabisulphite, and various amines used at a level of from 0.2% to 10 wt %. Suitable compounds that reversibly change oxidation state include various metal ions and their complexes, such as complexed ferric and ferrous ions used at a level of from 0.001% to 1.500 wt %. The presence of persulphates as oxidant is also preferred, such as ammonium or sodium persulphate at a level from 0.01 to 1.00 wt %, more preferably from 0.05% to 0.10 wt %. The polymerisation is performed under inert gas at, usually nitrogen, and typically at a temperature of from about 5° C. to 60° C. and more preferably between 35° C. and 50° C.

The hard polymer particles are derived from the same monomers as those used to produce the soft polymer particles. They may be autoxidisable, although preferably, they are non-autoxidisable for the sake of simplicity and cost. Amide moiety containing monomers, such as (meth)acrylamide may be used, preferably at levels up to 5 wt %, more preferably from 2 to 5 wt % based on the total monomer content.

Preferably, the monomer mixture substantially free of chain transfer agents.

More preferably, the hard polymer particles are of the core-shell type, by which is meant that the particles are prepared by sequentially polymerising at least two differing monomer compositions, usually of differing Tg. Whilst not wishing to be bound by this it is thought that the inner portion (core) and the outer portion (shell) form distinct regions. In any event, where the Tg of the core and shell differ, the Tg of the combined core and shell monomers should be calculated when considering the overall Tg of the polymer particles.

Preferably, the hard polymer particles are free of gel and/or autoxidisable moieties.

When the main monomer of the shell feed is more hydrophobic than the core monomer(s), a crosslinker, such as divinyl benzene is preferably added to the core feed to avoid obtaining inversed particles. By inverse is meant that the particles rearrange so that the shell polymer becomes the core and the core polymer becomes the shell. This is a particular problem when styrene is used as a major part of the shell polymer. Preferably from 2 to 8 wt % of the crosslinker should be added, more preferably from 2 to 6 wt %, even more preferably from 2 to 4 wt % and most preferably 2 wt % based on the total weight of core monomers.

Suitable crosslinkers include monomers with at least two copolymerisable moieties. Suitable such crosslinkers include divinyl benzene and allyl methacrylate.

N-methylol-acrylamide (NMA) can be included in the shell, in particular, to improve the hardness and to crosslink with the soft polymer particles.

The addition of crosslinker monomers such as divinyl benzene along with styrene in the second feed is necessary to obtain films that are simultaneously sandable after 4 hours and stain resistant after 1 day to water and water-based liquid stains.

Preferably, the varnish composition comprises from 0 to 1.5 wt % of volatile organic material, more preferably from 0 to 1 wt %, even more preferably from 0 to 0.5 wt % and most preferably the composition is free of volatile organic material.

Preferably, the composition is free of pigments, although matting agents-particles used to reduce the gloss of transparent coatings such as varnish—may be used. Such pigments preferably have a refractive index similar to the binder system itself in order to reduce any scattering of light and thereby preserve the transparency of the coating.

Typical matting agents include treated and untreated silica particles; waxes such as polythene, polypropylene, amide and carnauba; and small size inorganic fillers.

Coloured organic or inorganic pigments, including titanium dioxide, may also be used alone or with matting agents, to give some colour to the varnish. Solid non-film forming polymer particles are not regarded as pigments for the purposes of this invention.

A drier or siccative is preferably added to the aqueous dispersion to accelerate the autoxidative cross-linking and hardening of the coating. Such driers are generally organometallic compounds, typically transition metal carboxylates such as cobalt naphthenate. Other examples include manganese, lead, vanadium and zirconium compounds. Preferably the varnish contains at least one siccative.

The primary driers can be dissolved in organic solvent or in water and/or water compatible organic solvent depending on the solubility of the drier itself. Driers which are in aqueous solutions are preferred as they contribute little or not at all to VOC and they are more compatible with the final aqueous varnish.

The primary driers can be used in combination with other metal compounds comprising for example, calcium or potassium. Such metal compounds are referred to as secondary driers as they are not very efficient when used alone. They nevertheless, produce a synergistic effect when used in combination with the primary driers hereinbefore described.

Preferably, the driers are used at levels of from 0.05 to 0.60 wt %, more preferably from 0.05 to 0.25 wt % and most preferably from 0.075 to 0.20 wt % based on the non-vol resin content of the varnish The composition can further contain ingredients selected from the list consisting of antifoams, biocides, wetting and levelling agents and wax.

Suitable examples of antifoams include Surfynol MD-20 and DF-574, preferably from 0.01 to 0.1 wt % based on the varnish formulation.

Suitable biocides include Rocima V189.

Suitable wetting and levelling agents include Dynol 604.

Suitable waxes include Aquacer 513, preferably from 1 to 3 wt % based on the varnish formulation.

There is also provided an article coated with a varnish of the invention.

There is also provided a process of making an autoxidisable aqueous varnish of the invention comprising the steps of
a) providing a binder system comprising on a non-vol basis
i) 40-60 wt % soft autoxidisable polymer particles of Fox Tg less than 5° C. and comprising at least 60 wt % gel
ii) 60-40 wt % hard polymer particles of Fox Tg at least 40° C.
wherein the soft polymer particles are produced by polymerising a monomer mixture comprising at least one copolymerisable autoxidisable monomer, preferably using an emulsion polymerisation process b) providing a carrier liquid comprising at least 50 wt % water and an amount of volatile organic material comprising from 0 to 2 wt % when calculated on the total liquid varnish composition and c) optionally providing pigment at a pigment to binder weight ratio up to 0.05:1 calculated on a non-vol basis.

d) mixing the ingredients a), b) and c).

Test Methods

Gel Content

To determine the gel content of the copolymer, about 2 grams of the latex are accurately weighed into a 33 mL plastic centrifuge tube that is then filled up with 30 mL tetrahydrofuran and capped. The latex is dissolved by shaking the mixture for 30 minutes at ambient temperature in a shaker. Centrifugation for 2 hours at 35,000 G allows the gel to settle at the bottom of the tube. The clear liquid is then separated off from the solid gel blend, which is then dried in the oven first at 50° C. for 4 hours followed by another hour at 110° C. and subsequently weighed. The % gel content in the non-volatile (NV) latex fraction is defined as follows: (weight of gel/NV weight of sample)×100.

Sandability

The sandability is tested on wood panels dried at room temperature in a well ventilated laboratory environment. Early sandability is assessed after 4 hours drying. Each coat is applied either by brush (about 60 μm dry thickness) or with a bar coater (60 μm wet thickness, bar No. 6), then dried at room temperature (22° C.) for respectively 4 hours, and then overnight between coats.

The sandability is checked by hand-sanding with 3M P600 or P400 sand paper. Coatings are judged to be sandable when they form fine powder which does not clog the sandpaper.

Erichsen Hardness

An Erichsen Pendulum Hardness testing machine (Model 299/300) was used in accordance with ISO 1522:2001. The coating is applied on a glass panel (6×4 inches) with a paint block-spreader at a wet thickness of 100 μm. Then it is dried at room temperature (22° C.) during 1 hour before testing the hardness. Further measurements are made after 4 hours, 1 day, 4 days and 7 days of drying. Early hardness is considered to be between 1 hour and 1 day, final hardness is generally achieved between 4 days and 7 days.

Pencil Hardness

The pencil hardness is assessed according to ASTM D3363-92a. The scale, in increasing hardness, is 6B-5B-4B-3B-2B-B-HB-F-H-2H-3H-4H-5H. The pencil hardness is measured on the same coated glass panel used for the pendulum hardness after 7 days.

Stain Resistance

The stain resistance is tested on wood panels coated with 3 layers of coating. Each coat is applied either by brush (about 60 μm dry thickness) or with a bar coater (60 μm wet thickness, bar N° 6), then dried at room temperature (22° C.) for respectively 4 hours, and overnight between coats. The panels are lightly sanded between coats to remove any imperfections. The stain test is carried out after 1 day and 1 week of cure. Drops of various testing liquids are placed on the films and left at room temperature during 1 hour. The liquids are then removed with a humid rag and the damage to the coating is visually assessed on a scale from 1 to 5.1 means that the coating is severely damaged or coloured, 5 means that the coating is not affected without any mark or colouration. The testing liquids are the following: 1: water; 2: 50:50 ethanol: water mixture; 3: bleach solution; 4: liquid "Flash" (a commonly used U.K. detergent); 5: coffee; 6: tea; 7: wine; 8: shoe polish paste.

The invention will now be exemplified by the following examples.

EXAMPLES

Preparation of TOFA and SOFA Based Autoxidisable Monomers

GMA-TOFA Adduct 499.1 g (57.57%) of Sylfat 2 (TOFA, available from Arizona Chemical, PO Box 60053, 1320 AB Almere, The Netherlands), 11.3 g (1.30%) of tetraethylammonium bromide and 0.87 g (0.10%) of hydroquinone are charged under nitrogen to a one liter round bottom flask fitted with a reflux condenser and a stirrer. The contents of the flask are stirred and heated to 80° C. and then 355.7 g (41.03%) of glycidyl methacrylate is added gradually over a period of 2 hours whilst a temperature of 80° C. and stirring are maintained for a further 1.5 hours.

During the process, TOFA reacts with oxirane moieties in the glycidyl methacrylate to form a copolymerisable diester in which unsaturated methacrylate moieties are linked to an autoxidisable TOFA carboxylate by a hydroxypropylene divalent group. The reaction is catalysed by the tetraethylammonium bromide and premature polymerisation is inhibited by the hydroquinone. The resulting copolymerisable compound is a copolymerisable autoxidisable monomer and is stored at 4° C. until used. An excess of the glycidyl methacrylate over the TOFA is used.

GMA-SOFA Adduct

The recipe and method described to make the GMA-TOFA monomer described above was followed but with the TOFA replaced with the same amount of Sunflower oil fatty acid, Nouracid HE30 supplied by Brenntag NV, Netherlands.

Latex Preparation

Soft Polymer Latex Examples 1a & 2a

The aqueous polymer latices were prepared according to the formulation recipe (table 1) and the mini-emulsion method described below.

Method

To a 2 liter parallel sided reactor fitted with a stirrer, condenser, feed inlets and a nitrogen blanket were added the ingredients shown in Table 1 using the following mini-emulsion method:

1 Prepare the monomer emulsion using a Silverson homogeniser (Model LR2) at 10000 rpm for 20 minutes
2 Load the aqueous charge and 20% of the monomer emulsion prepared in 1 as a seed emulsion. Establish a nitrogen blanket and raise the temperature to 37° C.
3 Add seed oxidant solution, hold 10 minutes
4 Add 35% of the reductant solution and allow to exotherm
5 Raise temperature to 50° C. and hold for 20 minutes
6 Commence feeds with the remainder of the reductant solution and 80% of the monomer emulsion over 3 hours at a linear rate
7 Ten minutes before the end of feeds, add MFV rinse B, mix well and feed over 10 minutes
8 When feeds are complete, hold 10 minutes
9 Add oxidant mop-up solution, hold 10 minutes
10 Feed reductant mop-up solution over 30 minutes
11 After 10 minutes add spike 1, hold 30 minutes
13 Add spike 2, hold 30 minutes
14 Cool to 30 C and filter through 80 μm nylon mesh

TABLE 1

Formulation recipe of the autoxidative gel-containing dispersion a)

| Soft latex | 1a | 2a |
|---|---|---|
| Aqueous Charge | wt % | wt % |
| Water (mains) | 13.219 | 13.105 |
| Monomer Emulsion | | |
| Styrene Monomer | 6.504 | 6.448 |
| Methyl Methacrylate | 10.449 | 8.306 |
| 2-ethyl hexyl acrylate | 7.327 | 10.336 |
| Methacrylamide | 1.734 | 1.719 |
| GMA-TOFA adduct | 17.343 | 17.194 |
| Water (mains) | 27.928 | 27.687 |
| Disponil A4066 | 2.206 | 2.030 |
| MFV rinse B | | |
| Water (mains) | 4.655 | 4.615 |
| Seed Oxidant | | |
| Water (mains) | 0.165 | 0.163 |
| Ammonium Persulphate | 0.061 | 0.060 |
| Feed Oxidant | | |
| Water (mains) | 2.607 | 2.584 |
| Ammonium Persulphate | 0.183 | 0.182 |
| Reductant Solution | | |
| Water (mains) | 2.793 | 2.769 |
| SMBS | 0.279 | 0.277 |
| Oxidant Mop-up | | |
| Water (mains) | 0.726 | 0.720 |
| t-butyl hydroperoxide | 0.147 | 0.146 |
| Reductant Mop-up | | |
| Water (mains) | 0.907 | 0.899 |
| Sodium Meta Bi-Sulphite | 0.199 | 0.198 |
| Spike 1 | | |
| t-Butyl Perbenzoate | 0.049 | 0.049 |
| 10% NaAsc solution | 0.235 | 0.233 |
| Spike 2 | | |
| t-Butyl Perbenzoate | 0.049 | 0.049 |
| 10% NaAsc solution | 0.235 | 0.233 |
| | 100.000 | 100.000 |
| Tg | −6 | −15 |

Disponil A4066 is a non-ionic surfactant supplied by Cognis
NaAsc=Sodium Ascorbate
SMBS=Sodium metabisulphite Both latices 1a and 2a have the following parameters
nv=46 wt %
gel content=85%
mean particle size (diameter)=110 nm
pH=3.5
Minimum film forming temperature 1° C.
1.5% of a 5% cobalt acetate solution and 1.25% of a 10% potassium chloride solution was added to each latex, by weight calculated on the 100% latex recipe.

Comparative Soft Polymer Latex Examples 3a-6a

Comparative latices 3a-6a were prepared using the process and recipe as described for example 1a above except for the differences identified below:

Comparative Latex 3a

The monomer emulsion of Latex 1a (as described in Table 1) was replaced by that shown in Table 3 below. Note that the GMA/TOFA adduct is replaced by a mixture of MMA and EHA to achieve the same calculated Tg of −6° C.

TABLE 3

| Monomer Emulsion | wt % |
|---|---|
| Styrene Monomer | 6.559 |
| Methyl Methacrylate | 13.905 |
| 2-EHA | 21.513 |
| Methacrylamide | 1.749 |
| Water (mains) | 27.745 |
| Disponil A4066 | 2.186 |

The resulting latex 3a) has a solid content of 46%, a particle size of 135 nm (measured with a Malvern light scattering particle sizer), a pH of 3.5, and zero gel.

Comparative Latex 4a

This is identical to latex 1a but the drier system (cobalt acetate and potassium chloride) was not added to the latex.

Comparative Latex 5a

The monomer emulsion of 1a was replaced by that in Table 4 below where 1% (on monomer weight) of a chain transfer agent, n-octyl mercaptan, was added to reduce the molecular weight of the copolymer. Because the methacrylamide is thought to produce microgel, this compound was also omitted from the monomer emulsion. The Fox Tg was −6° C.

TABLE 4

| Monomer Emulsion | wt % |
|---|---|
| Styrene Monomer | 6.492 |
| Methyl methacrylate | 12.644 |
| 2-EHA | 6.842 |
| Methacrylamide | 0.000 |
| GMA-TOFA adduct | 17.32 |
| n-octyl mercaptan | 0.445 |
| Water (mains) | 27.82 |
| Disponil A4066 | 2.207 |

The resulting latex 5a has a solids content of 46%, a particle size of 131 nm (measured with a Malvern light scattering particle sizer), and a gel content of 0% (no gel).

Comparative Latex 6a

The monomer emulsion of 1a was replaced by that shown in Table 5 below, where the GMA/TOFA adduct is replaced with the GMA/SOFA adduct. The Fox Tg is −6° C. The methacrylamide was again removed from the monomer mixture for the reasons given above

TABLE 5

| Monomer Emulsion 6a | wt % |
|---|---|
| Styrene Monomer | 6.333 |
| Methyl Methacrylate | 12.355 |
| Ethyl Hexyl Acrylate | 6.646 |
| GMA-SOFA adduct | 16.890 |
| Water (mains) | 27.198 |
| Disponil A4066 | 4.762 |

The resulting latex has a solids content of 46%, a particle size of 131 nm (measured with a Malvern light scattering particle sizer), and a gel content of 2.9%.

Hard Polymer Latex

Examples 1b, 2b, 3b, 4b

The aqueous dispersions of hard polymer particles are produced using a conventional emulsion polymerisation process, adapted to produce core-shell type particles as described below.

The compositions of examples 1b-4-b are detailed in Table 2

TABLE 2

Formulation recipe of hard particle-containing dispersion b)

| Hard latex<br>Aqueous Charge | 1b<br>wt % | 2b<br>wt % | 3b<br>wt % | 4b<br>wt % |
|---|---|---|---|---|
| Demineralised Water | 43.10 | 42.36 | 42.59 | 42.60 |
| Kemsurf OS 38 | 0.23 | 0.23 | 0.23 | 0.23 |
| Sodium bicarbonate | 0.13 | 0.13 | 0.13 | 0.13 |
| Monomer (core) Seed | | | | |
| Methyl methacrylate | 1.69 | 0.00 | 1.69 | 4.41 |
| Butyl acrylate | 0.74 | 0.00 | 0.74 | 0.74 |
| 2-Ethyl hexyl acrylate | 0.02 | 0.00 | 0.02 | 0.02 |
| Styrene | 0.00 | 2.45 | 0.00 | 0.00 |
| AMPS Seed | | | | |
| Demineralised Water | 0.04 | 0.04 | 0.04 | 0.04 |
| Lubrizol 2405 | 0.04 | 0.04 | 0.04 | 0.04 |
| Initiator Shot | | | | |
| Demineralised Water | 1.00 | 1.00 | 1.00 | 1.00 |
| Potassium Persulphate | 0.19 | 0.19 | 0.19 | 0.19 |
| Monomore (core) Feed 1 | | | | |
| Methyl methacrylate | 15.22 | 0.00 | 15.22 | 37.00 |
| Butyl acrylate | 6.62 | 0.00 | 6.62 | 6.62 |
| 2-Ethyl hexyl acrylate | 0.22 | 0.00 | 0.22 | 0.22 |
| Styrene | 0.00 | 22.06 | 0.00 | 0.00 |
| Divinyl benzene | 0.00 | 0.00 | 0.50 | 0.50 |
| Monomer (shell) Feed 2 | | | | |
| Methyl methacrylate | 23.77 | 12.99 | 0.00 | 0.00 |
| 2-Ethyl hexyl acrylate | 0.00 | 11.52 | 0.00 | 0.00 |
| Styrene | 0.00 | 0.00 | 22.77 | 0.00 |
| Surfactant Feed | | | | |
| Demineralised Water | 3.26 | 3.26 | 3.26 | 3.26 |
| Kemsurf OS 38 | 0.28 | 0.28 | 0.28 | 0.28 |
| Lubrizol 2405 | 0.81 | 0.81 | 0.81 | 0.81 |
| N-methylol acrylamide 48% sol* | 0.74 | 0.74 | 0.74 | 0.00 |
| Reductant Shot | | | | |
| Demineralised Water | 0.93 | 0.93 | 0.93 | 0.93 |
| sodium formaldehyde sulfoxylate | 0.02 | 0.02 | 0.02 | 0.02 |
| Oxidant Shot | | | | |
| Demineralised Water | 0.93 | 0.93 | 0.93 | 0.93 |
| t-butyl hydroperoxide | 0.02 | 0.02 | 0.02 | 0.02 |
| | 100.00 | 100.00 | 100.00 | 100.00 |

| | Core | | Shell | | Cross- |
|---|---|---|---|---|---|
| | Tg | main | Tg | main | linker |
| 1b | 34 | MMA | 105 | MMA | NMA |
| 2b | 100 | ST | -4 | MMA | NMA |
| 3b | 34 | MMA | 100 | ST | DVB/NMA |
| 4b | 65 | MMA | — | — | None |

*NMA is added to 2nd part of surfactant feed after 2hrs

Kemsurf OS 38 is a sodium C14-16 Olefin Sulphonated surfactant supplied by Lankem
Lubrizol 2405 is a 2-acrylamido-2-methylpropane sulfonic acid (AMPS) monomer supplied by Lubrizol
Method
1 Charge reactor with the Aqueous charge and begin nitrogen sparge and raise temperature to 78° C.
2 Add Monomer (core) seed, AMPS seed, hold 10 minutes and switch from sparge to nitrogen blanket.
3 Add initiator shot, allow to exotherm and hold for 30 minutes
4 Add Monomer (core) feed 1 over 2 hours and surfactant over 4 hours
5 After 2 hours switch to Monomer (shell) feed 2.
6 Add N-methylol acrylamide to surfactant feed if required and feed in over 2 hours
7 Hold on temperature for 30 minutes then add reductant and oxidant shots and hold for a further 20 minutes Dispersions 1b-4b all have solid content of 50% and particle size of 110 to 120 nm (measured with a Malvern light scattering particle sizer).

Preparation of Varnish Compositions

Varnish Examples 1 to 4

The varnishes are blends of the soft and hard polymer dispersions, 50 parts of the selected soft latex a is blended with 50 parts of the selected hard latex b to make a 50:50 blend composition. This ratio can be adjusted up to 60:40 if necessary for higher early and final hardness. Numerous blend combinations can be made; here the following blends have been prepared using the dispersions soft and hard dispersions described above.
The blends are all by weight of dispersion.
Varnish Example 1 is a 1:1 mixture of latex 1a and latex 1b
Varnish Example 2 is a 1:1 mixture of latex 2a and latex 2b
Varnish Example 3 is a 1:1 mixture of latex 1a and latex 3b
Varnish Example 4 is a 45:55 mixture of latex 1a and latex 4b Comparative Varnish Examples 5-9

The comparative varnish examples 5-9 consisted of the same hard latex 1b blended 1:1 with the comparative soft latex described above. The varnishes were produced as before by blending the soft and hard latices in a weight ratio of 1:1, except for Comparative varnish 9, where the soft latex was used on its own.

| Comparative varnish | soft particle latex | hard particle latex |
|---|---|---|
| 5 | 3a | 1b |
| 6 | 4a | 1b |
| 7 | 5a | 1b |
| 8 | 6a | 1b |
| 9 | 1a | none |

Evaluation of Varnishes 1-9
Erichsen Hardness
The hardness results are given in Erichsen seconds. The pencil hardness is measured after 1 month (final hardness) (see table 6).

TABLE 6

Hardness results (pendulum and pencil) of the examples 1 to 8

| Example # | 1 | 2 | 3 | 4 | 5 | 6 | 7 | 8 | 9 |
|---|---|---|---|---|---|---|---|---|---|
| 1 hr hardness/s | 76 | 65 | 72 | 74 | 64 | 55 | 42 | 45 | 16 |
| 4 hr hardness/s | 81 | 92 | 86 | 83 | 70 | 61 | 50 | 51 | 16 |
| 1 day hardness/s | 109 | 109 | 118 | 108 | 71 | 64 | 82 | 64 | 60 |
| 4 days hardness/s | 143 | 136 | 138 | 140 | 76 | 71 | 104 | 94 | 93 |
| 7 days hardness/s | 156 | 150 | 160 | 153 | 76 | 71 | 112 | 117 | 99 |
| Pencil hardness | F | F | F | F | F | B | F | F | F |

The examples 1 to 4 demonstrate a good early hardness (between 70 and 100 Erichsen seconds) and a good final hardness (between 140 and 170 sec), whereas the non-autoxidisable example 5, and the non-curing example 6 demonstrate a poor final hardness (below 80s). The non-microgel-containing examples 7 and 8, and the blend-free example 9 demonstrate a poor early hardness (below 50s).

Thus, good early and final hardnesses can only be achieved with blends comprising an autoxidisable microgel-containing dispersion and a hard particle-containing dispersion.

The coated panels are then handleable in less than 4 hours. The sandability of examples 1 to 4 is excellent after 4 hours, they are very easy to sand and they can be easily recoated with a second layer of varnish. Examples 5 to 9, however, are difficult to sand and block the sandpaper during sanding and are thus unacceptable.

1.1 Stain Resistance

The stain resistance is evaluated on autoxidisable microgel-containing blend samples after 1 day and 7 days. Example 2 is evaluated against the non-curing comparative example 5 as follows (see table 7)

TABLE 7

Stain resistance results for examples 2 and 5

| Example # | Time *(days) | Water | Ethanol | Bleach | Flash |
|---|---|---|---|---|---|
| 2 | 4 hrs | 5 | 5 | 5 | 5 |
| 2 | 1 | 5 | 5 | 5 | 5 |
| 2 | 7 | 5 | 5 | 5 | 5 |
| 3 | 4 hrs | 5 | 5 | 5 | 5 |
| 3 | 1 | 5 | 5 | 5 | 5 |
| 3 | 7 | 5 | 5 | 5 | 5 |
| 5 | 4 hrs | 4 | 4 | 4 | 4 |
| 5 | 1 | 4 | 4 | 4 | 4 |
| 5 | 7 | 4 | 4 | 4 | 4 |

| Example # | Time (days) | Coffee | Tea | Red Wine | Shoe Polish |
|---|---|---|---|---|---|
| 2 | 4 hrs | 5 | 5 | 5 | 5 |
| 2 | 1 | 5 | 5 | 5 | 5 |
| 2 | 7 | 5 | 5 | 5 | 5 |
| 3 | 4 hrs | 5 | 5 | 5 | 5 |
| 3 | 1 | 5 | 5 | 5 | 5 |
| 3 | 7 | 5 | 5 | 5 | 5 |
| 5 | 4 hrs | 2 | 3 | 1 | 4 |
| 5 | 1 | 2 | 3 | 1 | 4 |
| 5 | 7 | 3 | 4 | 1 | 5 |

*unless otherwise stated

The results clearly show the good early and final water-based-stain resistance for Varnish Example 2 of the present invention compared to the non-autoxidisable comparative Varnish Example 5.

The film made with the example 3 surprisingly demonstrates a unique performance in both early sandability after 4 hours of drying at room temperature and early stain resistance after 1 day of drying, being also hard and clear.

The invention claimed is:

1. An autoxidisable aqueous varnish composition comprising
   a) film forming polymer latex binder system comprising, on a non-vol basis
      i) 40-60 wt % soft autoxidisable polymer particles of Fox Tg less than 5° C.
      ii) 60-40 wt % hard polymer particles of Fox Tg at least 40° C.
      wherein the soft autoxidisable polymer particles comprise at least 60 wt % gel,
   b) a carrier liquid comprising at least 50 wt % water and an amount of a volatile organic material of from 0 to 2 wt % when calculated on the total liquid varnish composition, and
   c) optionally pigment at a pigment to binder weight ratio up to 0.05:1.

2. The varnish composition according to claim 1 wherein the composition is free of volatile organic material.

3. The varnish composition according to claim 1 wherein the soft polymer particles comprise at least 30 wt % of autoxidisable monomer.

4. The varnish composition according to claim 1 wherein the autoxidation capability is provided by an adduct of glycidyl methacrylate and unsaturated fatty acid.

5. The varnish composition according to claim 4 wherein the fatty acid contains at least two double bonds.

6. The varnish composition according to claim 5 wherein at least some of the double bonds are conjugated.

7. The varnish composition according to claim 6 wherein the minimum amount of conjugated unsaturated fatty acid in the unsaturated fatty acid mixture is from 1.5 to 15 wt %.

8. The varnish composition according to claim 4 wherein the unsaturated fatty acid is tall oil fatty acid.

9. The varnish composition according to claim 4 wherein the unsaturated fatty acid is a $C_{10}$-$C_{24}$ unsaturated drying or semi-drying acid.

10. The varnish composition according to claim 1 wherein the soft polymer comprises from 2 to 6 wt % of an amide monomer.

11. The varnish composition according to claim 1 wherein the hard polymer particles are substantially free of gel.

12. The varnish composition according to claim 1 wherein the hard polymer particles are of the core-shell type.

13. The varnish composition according to claim 12 wherein the shell monomers comprise from 2 to 6 wt % of a crosslinker monomer.

14. The varnish composition according to claim 1 and further containing at least one siccative.

15. The varnish composition according to claim 1 which is free of pigment.

16. A process of preparing an autoxidisable aqueous varnish according to claim 1 comprising the steps of
   a) providing a binder system comprising on a non-vol basis
      i) 40-60 wt % soft autoxidisable polymer particles of Fox Tg less than 5° C. and comprising at least 60 wt % gel
      ii) 60-40 wt % hard polymer particles of Fox Tg at least 40° C.
      wherein the soft polymer particles are produced by polymerising a monomer mixture comprising at least one copolymerisable autoxidisable monomer,
   b) providing a carrier liquid comprising at least 50 wt % water and an amount of volatile organic material comprising from 0 to 2 wt % when calculated on the total liquid varnish composition,
   c) optionally providing pigment at a pigment to binder weight ratio up to 0.05:1 calculated on a non-vol basis, and
   d) mixing the ingredients a), b) and c).

17. The process of claim 16 wherein the soft polymer particles are produced using an emulsion polymerisation process.

18. An article coated with a varnish according to claim 1.

* * * * *